United States Patent
Palpanas et al.

(10) Patent No.: US 11,471,113 B2
(45) Date of Patent: Oct. 18, 2022

(54) DETERMINATION OF HEALTH STATUS OF SYSTEMS EQUIPPED WITH SENSORS

(71) Applicants: UNIVERSITÉ DE PARIS, Paris (FR); ÉLECTRICITÉ DE FRANCE, Paris (FR)

(72) Inventors: Themis Palpanas, Paris (FR); Michele Linardi, Paris (FR); Paul Boniol, Paris (FR); Federico Roncallo, Paris (FR); Mohammed Meftah, Aulnay sous Bois (FR); Emmanuel Remy, Paris (FR)

(73) Assignees: UNIVERSITÉ DE PARIS, Paris (FR); ÉLECTRICITÉ DE FRANCE, Paris (FR)

( * ) Notice: Subject to any disclaimer, the term of this patent is extended or adjusted under 35 U.S.C. 154(b) by 0 days.

(21) Appl. No.: 17/229,899

(22) Filed: Apr. 14, 2021

(65) Prior Publication Data
US 2021/0321956 A1 Oct. 21, 2021

(30) Foreign Application Priority Data
Apr. 20, 2020 (FR) ...................................... 2003946

(51) Int. Cl.
*G06F 13/00* (2006.01)
*A61B 5/00* (2006.01)
*A61B 5/346* (2021.01)
*G01M 99/00* (2011.01)

(52) U.S. Cl.
CPC ............ *A61B 5/7282* (2013.01); *A61B 5/346* (2021.01); *A61B 5/7264* (2013.01); *G01M 99/005* (2013.01)

(58) Field of Classification Search
CPC .................................................... A61B 5/7282
See application file for complete search history.

(56) References Cited

U.S. PATENT DOCUMENTS 10,699,040 B2 * 6/2020 Martin ................ G07C 5/0825

OTHER PUBLICATIONS

Boniol et al.: "Automated Anomaly Detection in Large Sequences", 2020 IEEE 36th International Conference On Data Engineering (ICDE), 2020. pp. 1834-1837 (Year: 2020).*

(Continued)

*Primary Examiner* — Phuong Huynh
(74) *Attorney, Agent, or Firm* — Pearne & Gordon LLP

(57) ABSTRACT

A method for determining a health status of a system of interest is proposed. The method comprises acquiring (S1) a time series, extracting (S2) subsequences, selecting (S3) a set of subsequences, classifying (S4) the subsequences of the set into several groups on the basis of at least one criterion of resemblance to at least one reference subsequence, and constructing (S5) a normal operating model of the system of interest. The construction includes, for each group, a modeling (S51) of a representative subsequence and a determination (S52) of an associated weight. The normal model is defined by the modeled subsequences and the associated weights. The method further includes an attribution (S6) of a normality score to each subsequence extracted by comparison with the normal model, an identification (S7) of at least one abnormal subsequence, and a determination (S8) of the health status of the system of interest.

20 Claims, 4 Drawing Sheets

(56) References Cited

OTHER PUBLICATIONS

Boniol et al., "SAD: An Unsupervised System for Subsequence Anomaly Detection." 36th International Conference on Data Engineering (ICDE) 2020. pp. 1778-1781 (Year: 2020).*
Preliminary search report ("Rapport de Recherche Preliminaire") issued in corresponding French Application No. FR2003946 dated Jan. 20, 2021, 9 pages.
Boniol, et al. "Automated Anomaly Detection in Large Sequences." 36th International Conference on Data Engineering (ICDE) 2020. pp. 1834-1837.
Boniol, et al. "SAD: An Unsupervised System for Subsequence Anomaly Detection." 36th International Conference on Data Engineering (ICDE) 2020. pp. 1778-1781.
Rodpongpun, et al. "Selective Subsequence Time Series Clustering." Knowledge-Based Systems. vol. 35. 2012. pp. 361-368.
Farahani, et al. "Time Series Anomaly Detection from a Markov Chain Perspective." 18th IEEE International Conference on Machine Learning and Applications (ICMLA). 2019. pp. 1000-1007.
Boniol, et al. "Series2Graph: Graph-based Subsequence Anomaly Detection for Time Series." Proceedings of the VLDB Endowment. vol. 13, No. 12, 2020 pp. 1821-1834.
Boniol, et al. "Unsupervised Subsequence Anomaly Detection in Large Sequences." Proceedings of the VLDB 2020 PhD Workshop. Aug. 31, 2020. 4 pages.

\* cited by examiner

US 11,471,113 B2

DETERMINATION OF HEALTH STATUS OF SYSTEMS EQUIPPED WITH SENSORS

TECHNICAL FIELD

The present disclosure is in the field of data science.

More particularly, the present disclosure relates to methods for determining health status of sensor-equipped systems, as well as computer programs, computer-readable devices for storing, and processing circuits for the application of such methods.

PRIOR TECHNIQUE

The surveillance of an equipment in operation consists in setting up a system which reports in real time on the statu of the equipment. Very classically, the equipment is equipped with sensors, in particular digital sensors that measure physical parameters (a flow rate, a pressure, a temperature, a number of beats per minute, etc.).

The measurements of these sensors can therefore be stored and analyzed, mainly in the form of time series, which are sequences of time-stamped values.

The analysis of these time series, in particular the detection of anomalies, thus makes it possible to watch out the statu of the equipment and, if necessary, to launch alarms when the equipment leaves the normal operating range, which can have consequences on the operation such as production blockages, premature wear or others.

The detection of anomalies in large time series, typically in time series formed by data accumulated over several years with a granularity of the order of a second, is an important problem finding applications in a large number of fields, including in particular:

aeronautics, automotive and railways, e.g. for the surveillance of the operation of vehicles, smart cities and factories, e.g. for power consumption forecasting, the Internet of things, e.g. for the detection of gestures and movements from a connected watch, industrial internet of things, e.g. for the surveillance of the functioning of an industrial device or system, such as a production line gathering several devices, or an industrial site such as a factory or a group of such sites, systems for controlling such as SCADA systems, e.g. integrated in power generation sites, health, e.g. for the surveillance of a physiological parameter such as cardiac activity or sleep activity, economy and finance, e.g. for fraud detection, systems of telecommunications and information, e.g. for data center management, cybersecurity, e.g. for intrusion detection, web services, e.g. for analyzing user web sessions to detect new behaviors, and law, e.g., for analysis of legal cases and characterization of discriminating elements.

It is then desirable to detect, among data samples from a time series, each sample being formed of a sub-sequence of time-stamped values extracted from the time series, those deviating from a norm and thus constituting anomalies.

Several known anomaly detection methods can be applied either directly to the data samples without any preliminary preprocessing, or by relying on a discrete representation of the time series.

It is indeed known to define a representation space, using a minimal number of variables, in which the data samples can be represented and classified. Various known methods allow to define such a representation space, including discrete Fourier transforms, wavelet transforms, singular value decompositions using principal component analysis, piecewise linear function approximations such as SAX, etc. These methods allow to transform each data sample obtained into a set of n values. It is then possible to graphically represent the set of data samples as a scatterplot in an n-dimensional space, each point corresponding to a data sample. The similarity between two data samples can be expressed as the Euclidean distance between the two points corresponding to these two samples in the n-dimensional space. The smaller this distance, the more similar the two samples are.

A known anomaly detection method is to detect data samples whose Euclidean distance to their nearest neighbor in n-dimensional space is the largest. This method is based on the notion of discord. The notion of discord of a time series T is defined as follows. Among all subsequences of size l in T, the discord of T is the subsequence $T_{i,l}$ that has the largest distance to its nearest neighbor. Formally, the nearest neighbor is defined as follows: $NN(T_{i,l},T)=\text{argmin}_{j\in[0,|T|],i\neq j}(\text{dist}(T_{i,l},T_{j,l}))$. The discord is therefore defined as follows: $\text{discord}(T)=\text{argmax}_{T_{i,j}}(NN(T_{i,l},T))$. An illustration of this definition is shown in FIG. 1. In this figure, a dot symbolizes a subsequence of T. Three groups of subsequences are shown as well as an isolated subsequence $T_{i,l}$. Although the information that the notion of discord provides is useful and interesting in some use cases, approaches using it fail once the time series of interest contains several similar anomalous samples. Here, only isolated anomalous subsequences, such as the subsequence $T_{i,l}$ can be detected by their distance di from their nearest neighbor. Recurrent anomalies $T_{j,l}$ or $T_{k,l}$ with a relatively small distance $d_j$ or $d_k$ to their nearest neighbor remain undetected.

The notion of $m^{th}$ Discord has been proposed to solve this problem. The notion of $m^{th}$ Discord of a time series T is defined as follows. Among all subsequences of size l in T, the $m^{th}$ Discord of T is the subsequence $T_{i,l}$ that has the largest distance to its $m^{th}$ nearest neighbor. An illustration of this definition is shown in FIG. 2. In this figure, a dot symbolizes a subsequence of T. As in FIG. 1, three groups of subsequences are shown there as well as an isolated subsequence $T_{i,l}$. If the 3rd Discord of T, i.e., the distance between each subsequence and its third-nearest neighbor, is chosen as the parameter defining a subsequence abnormality, then each isolated subsequence $T_{i,l}$, each isolated pair of subsequences, and each isolated triplet $T_{k,l}$ of subsequences are detected as abnormalities by their distance $d_{i,3}$, $d_{k,3}$. In contrast, groups of subsequences $T_{j,l}$ comprising more than three subsequences, thus having a relatively small distance $d_{j,3}$ to their third nearest neighbor, are not detected as anomalies.

The previous two notions can be grouped into the notion of Top k $m^{th}$ Discord, defined as follows. A subsequence $T_{i,l}$ is the Top k $m^{th}$ Discord of T if it has the $k^{th}$ largest distance to its $m^{th}$ nearest neighbor. Therefore, the discord of T is also the Top 1 $1^{st}$ Discord. Moreover, $m^{th}$ Discord of T is denoted by Top 1 $m^{th}$ Discord. In general, the known methods relying on the notion of $m^{th}$ Discord aim of searching for subsequences with the $m^{th}$ most distant nearest neighbor. However, these methods are very sensitive to the change of value of the parameter m. Small variations of this parameter can cause the appearance of false positives, i.e. subsequences detected as abnormal when they are not.

The above methods do not cover all possible cases of anomaly detection. In the case where the number of anomalies is not known (in addition to the majority of cases, including those concerning the detection of material failure of sensors in their operating history), and in the case where the anomalies are repeated (and thus each anomaly having a very close neighbor), the methods using these definitions do not work optimally. They either have difficulty providing a reliable answer (with a low rate of correct detections) or require a high computational time.

Other methods in the field of outlier detection, not specifically dedicated to the time series domain, are known. Methods based on the Local Outlier Factor (LOF) are examples of such known methods. Similar to the $m^{th}$ Discord methods, the Local Outlier Factor methods include a step of calculating a degree measuring the neighborhood density of each subsequence. This method requires a parameter k indicating the number of neighbors to consider when measuring the neighborhood density.

Similarly, other known methods aim to evaluate the isolation of each subsequence. This isolation is measured by constructing random binary trees dividing the space of subsequences of the time series in question in half at each node, until only one subsequence is obtained in each area of the space. The depth of the tree is used to construct a score indicating which subsequences are considered abnormal. The greater the depth to reach the subsequence to be evaluated, the more the subsequence in question is considered normal. Conversely, the shorter the depth, the more abnormal the subsequence will be considered. With the aim of homogenizing and stabilizing the score, several random trees are constructed and an average score is established.

As previously mentioned, these methods are not specifically dedicated to time series subsequences, so they fail in some of the cases tested during our experimental evaluation. Not being able to detect all types of anomalies is detrimental because the statu of the system under study is then not precisely monitored. Thus, the ability to predict premature wear, failure or degradation is negatively affected.

Finally, solutions using deep machine learning methods, more specifically recurrent neural networks, have recently been proposed. A drawback of these methods is that the correct detection rate is only optimized if examples of normal subsequences, or in some cases examples of different types of anomalies, are previously provided and identified as such. These methods therefore require prior supervision, which is a hindrance to their diffusion.

The approaches that have been proposed so far in the literature for the detection of anomalies in time series, for example from sensors, gathering measurements of a physical parameter over time, have serious limitations: either they require prior knowledge of the domain, or they become cumbersome and expensive to use in situations where recurrent anomalies of the same type occur.

There is therefore a need to be able to detect a large number of types of operating anomalies in a generic and scalable way, adaptable to the monitoring of any system equipped with a sensor capable of measuring a value indicative of a current operating status of the system. It is desirable that the detection is reliable, i.e. that both malfunctions and normal operations are correctly identified as such. It is also desirable that the detection does not require any supervision.

SUMMARY

This disclosure improves the situation.

A method of determining a health status of a system of interest equipped with at least one sensor is proposed, the method comprising:

an acquisition of a time series formed of a sequence of measurements from the sensor as a function of time, an extraction of a plurality of subsequences from the time series, each extracted subsequence being formed of a plurality of measurements, consecutive in time, extracted from said sequence of measurements, a selection of a set of subsequences, the set forming a part of the plurality of extracted subsequences, a classification of the subsequences of the selected set into several groups of subsequences on the basis of at least one criterion of similarity between each subsequence of the selected set and at least one reference subsequence, a construction of a normal operating model of the system of interest, the construction comprising, for each group of subsequences, a modeling of a subsequence representative of the subsequences of said group and a determination of a weight associated with the modeled subsequence by comparing a collective distribution of the subsequences forming said group with a collective reference distribution, the normal operating model of the system of interest being defined by the modeled subsequences and the associated weights, an attribution of a normality score to each extracted subsequence, based on a comparison between said extracted subsequence and the normal operating model of the system of interest, an identification of at least one abnormal subsequence, indicating an abnormality in the functioning of the system of interest, based on the assigned normality scores, and based on the at least one identified abnormal subsequence, a determination of the health status of the system of interest.

Since the sensors report on the status of the equipment, one objective is to be able to monitor the functioning of the equipment (or more broadly of a subject, for example a human in medicine). The detection of possible anomalies thus informs on the status of health of the material and can have as a consequence the activation of alarms which can require an action of correction or repair a posteriori. It can also help to increase the knowledge of the different operating modes of the equipment, whether these operating modes are already known or not. By "determination of health status" is meant, for example, the determination of a normal or non-normal operating status of the system of interest, or the determination of a faulty or non-faulty status of the system of interest. The method makes it possible to determine this status on the basis of an analysis of at least one series of measurements of one or more physical quantities of the system of interest acquired by the sensor or sensors with which it is equipped.

An intended objective is to detect measurement anomalies in a sensor to determine a health status of the sensor. The health status thus determined can give alerts and can lead to actions for correcting measurements, repairing the sensor, predicting or anticipating a need for maintenance of the sensor, enriching a database relating to the operation of sensors of the same type . . . .

The proposed method is based on the construction of a normal operation model and its use to detect anomalies. Surprisingly, it was found that the advantages of the proposed method, compared to known methods based on the concept of discord or $n^{th}$ discord, are:

a. better reliability, b. a reduced computation time which leads to a better scalability, and c. the fact that the method is agnostic, requiring no supervision or prior knowledge of normal operating ranges, which allows industrial applications in various technical domains.

The features outlined in the following paragraphs can optionally be implemented. They can be implemented independently of each other or in combination with each other.

In one example, the method includes, in conjunction with selection, an exclusion in which each subsequence whose proportion exceeding a predetermined threshold, is found in its entirety in at least one other subsequence is discarded from the selected set. Thus, any bias related to redundant consideration of the same portion of a time series is avoided.

In one example, the selection is a random selection of subsequences from the plurality of subsequences. Such a random selection has the advantage of requiring minimal computational time, yet is not detrimental to the quality of anomaly detection in large time series, according to initial experimental tests.

In one example, the selection is based on a comparison of the subsequences of the plurality of subsequences to each other, the set being formed such that each subsequence in the set has a degree of similarity exceeding a predetermined threshold to at least one other subsequence in the set. Such selection forces the formation of groups between subsequences that are statistically more similar than the average of the extracted subsequences, thus facilitating the relevant identification of recurrent types of behaviors of the system of interest.

In one example, the similarity criterion between a given subsequence A and a reference subsequence B results:

a determination of a distance dist(A, B) between the given subsequence and the reference subsequence, where the distance dist(A, B) is defined as $$dist(A, B) = \sqrt{\sum_{i=1}^{|A|} \left( \frac{A_{i,1} - \mu_A}{\sigma_A} - \frac{B_{i,1} - \mu_B}{\sigma_B} \right)^2},$$

where $A_{i,1}$ and $B_{i,1}$ denote a first measurement in time, $\mu_A$ and $\mu_B$ denote a mean, and $\sigma_A$ and $\sigma_B$ denote a standard deviation of the first subsequence A and the second subsequence B respectively, and a comparison of the determined distance with a reference value.

Such a normalized distance makes it possible to quantify the similarity between two subsequences. It is also possible, for example, to rank different subsequences in order of greatest similarity to a reference subsequence.

In one example, the ranking is based on a hierarchical clustering of the subsequences in the set, the hierarchical clustering being performed by repeating the following steps until a stopping criterion is reached:

determine, for each pair of subsequences in the set, a degree of similarity, form a group of level i, where i represents the number of subsequences in the set, based on the similarity criterion such that the group of level i consists of the pair of subsequences in the set with the highest determined degree of similarity, generate a subsequence representative of said level group i, intermediate between the subsequences of said level group i, and reduce the set by replacing the pair of subsequences forming said level group i with the generated subsequence representative of said level group i.

Thus, it is possible to represent all subsequences of the set by an n-level dendrogram, where the passage from level i to level i+1 corresponds to a reduction of the set by one unit, by replacing a pair of subsequences by a generated subsequence representing it.

In one example, during each iteration of the following steps, prior to performing each set reduction, the subsequences forming the set are encoded and the total memory size of the encoded subsequences is determined, and the stopping criterion is based on a comparison of the determined total memory size for two consecutive iterations of the following steps. Thus, the size of each group is chosen in such a way as to gather in the same group sub-sequences indicating the same recurrent normal operating mode of the sensor. Moreover, the hardware requirements in terms of memory space required for the implementation of the method are optimized.

In one example, in modeling a subsequence representative of the subsequences of said group, the modeled subsequence is intermediate between the subsequences of said group. For example, the modeled subsequence may be the iso-barycenter of the original subsequences forming the group, thus being equi-representative of the subsequences of said group. Thus, the modeled subsequence representative of a group of subsequences corresponding to a typical behavior of the system of interest may optionally be viewed as an average, typical, or debruited signal corresponding to that typical behavior.

In one example, the weight of each group is based on the number of subsequences forming said group. Indeed, the more recurrent the number of subsequences forming a given group, the more recurrent the associated behavior of the system of interest.

In one example, the weight of each group is based on a temporal coverage of said group. In other words, since each extracted subsequence has a temporal index, the weight of each group here is based on the indices of the subsequences forming said group. The larger the difference between the maximum and minimum index of the subsequences forming the group, the more the subsequences forming the group represent recurrent behavior of the system of interest over a long period of time.

In one example, the weight of each group is based on a centrality of said group relative to several groups. In other words, a given recurrent behavior of the system of interest is considered more central the more similar it is to a maximum of other recurrent behaviors of the system of interest.

In one example, the normality score of a given subsequence is obtained based on a comparison of the given subsequence with each subsequence of the normal model and based on a weighting of the results of said comparisons by the respective weights associated with each subsequence of the normal model. Surprisingly, it has been found that the combination of this comparison and weighting further increases the relevance of detecting atypical, or statistically abnormal, behavior as compared to other known methods.

In one example, the determined health status is used to generate an alert indicating a failure of the system of interest. Such an alert may include, for example, issuing a visual signal, an auditory signal, or a control signal from the system of interest.

In one example, the determined health status is used to correct subsequent measurements received from the sensor. Such a correction is used to compensate for an observed drift of the sensor while the system of interest does not otherwise exhibit any abnormality.

In one example, the determined health status is used to predict a subsequent change in the health status of the system of interest. Such a prediction may be useful, for example, in scheduling maintenance actions.

In one example, the determined health status is used to feed a database of health status of systems of a type similar to the system of interest. In effect, the determined health status for a given system of interest can be compared to similarly determined health status for a fleet of systems of interest.

Also proposed is a computer program having instructions for implementing the foregoing method when such program is executed by a processor.

Also provided is a non-transitory computer-readable recording medium having recorded thereon a program for implementing the foregoing method when such program is executed by a processor.

Also proposed is a processing circuit comprising a processor connected to the above non-transitory recording medium.

BRIEF DESCRIPTION OF THE DRAWINGS

Other features, details and advantages will become apparent from the detailed description below, and from an analysis of the attached drawings, in which.

DESCRIPTION OF THE METHODS OF REALIZATION

The following drawings and description contain, for the most part, matters of certainty. Therefore, they may not only serve to further the understanding of the present disclosure, but also contribute to its definition, if any.

Many systems are equipped with sensors for measuring quantities indicative of their operation in the form of time series that are sequences of time-stamped values.

For example, in an industrial plant, a pump is equipped with a flow sensor that reports the output speed of a fluid. In medicine, a patient may be equipped with an electrocardiograph to report cardiac activity (in particular heart rate).

These systems can be equipped with processing circuits to store and process the measurements locally. With the emergence of so-called intelligent and communicating systems, it is also possible to transmit the acquired measurements to a remote processing circuit for centralized processing. The processing of the acquired measurements can be used to qualify the operation of the system in question.

For example, considering as a system an industrial device that has to follow a pre-programmed temperature cycle and considering as an associated sensor a temperature probe, an objective can be to detect on the basis of temperature measurements by the sensor whether the industrial device is functioning correctly. Ideally, this detection is implemented automatically and without prior knowledge of the pre-programmed temperature cycle.

For example, considering a person or animal as a system and considering an electrocardiograph as an associated sensor, an objective may be to detect based on electrocardiograms whether the electrical activity of the heart of the person or animal is normal. Ideally, this detection is implemented automatically and unsupervised, including without first providing examples of normal electrocardiograms or electrocardiograms with abnormal characteristics.

An example of such a processing circuit is shown in the figure. The processing circuit shown includes a processor PROC (100) connected to a non-transitory recording medium MEM (200) on which is recorded a program for implementing a method as described below when that program is executed by the processor PROC (100).

Figure 8:
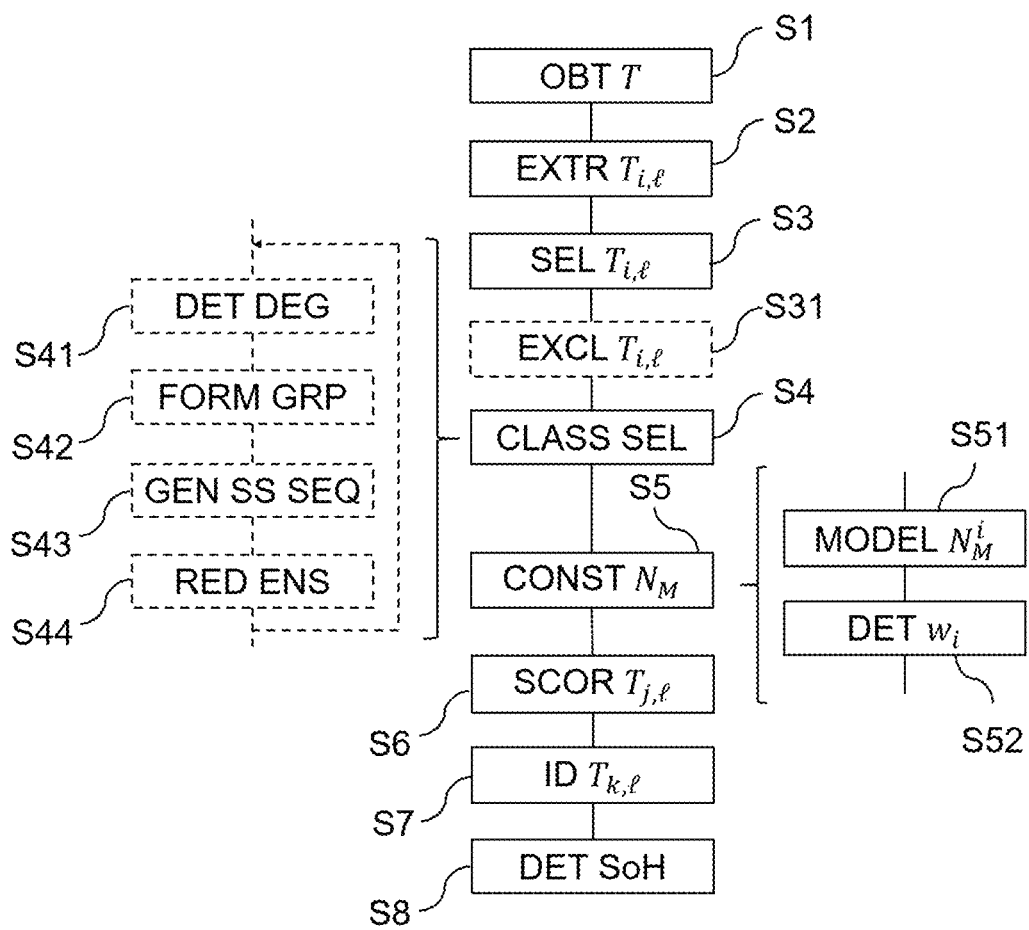
FIG. 8 represents a flow chart of a general algorithm of a computer program, in a particular example embodiment, for implementing the proposed determination method.

Reference is now made to FIG. 8, which illustrates an example embodiment of a method for determining a health status of a sensor-equipped system of interest. In this example, the system of interest is the road network of a city. The sensor is a counter of a number of rides provided by all cabs operating in the city's road network.

A time series T, formed by a sequence of measurements from the sensor as a function of time, is acquired OBT T (S1). Here, the acquired time series is a history of time-stamped measurements, spaced by a regular time interval, each measurement corresponding to the number of runs provided during the previous time interval. The size of the time series T, i.e. the total number of measurement points, is noted |T|. The resulting time series is then processed to determine, as the "health of the system of interest", whether the road traffic is normal or abnormal during a given time period with respect to the usual road traffic.

It should be noted that, of course, in various industrial applications, many systems of interest are equipped with a plurality of sensors and configured to acquire a time series from each sensor. Although the determination method allows for the processing, together or separately, of multiple time series, it is considered in this example embodiment, for simplicity, the processing of a single time series to determine the health status of a system of interest.

A plurality of subsequences $T_{i,l}$ (300) are extracted EXTR Ti,l (S2) from the time series T. The extracted subsequences $T_{i,l}$ (300) are subsets of consecutive measurement points within the time series. Each subsequence $T_{i,l}$ begins at index i, the $i^{th}$ point in T, and contains the l points that follow. Therefore, a given subsequence $T_{i,l}$ has size l and a single point in T can be seen as a subsequence of size 1. For example the point in the time series T with index i can alternatively be denoted $T_{i,1}$, or $T_i$.

In the example considered, each subsequence thus extracted may correspond to a fixed number of consecutive measurements, for example of the order of 10, 20, 50, or 100 measurements, within a time sequence covering several months or years, with a measurement step of, for example, the order of fifteen minutes, thirty minutes, or one hour.

At this stage, a preprocessing of the extracted subsequences can be performed to make the information contained in the subsequences less redundant and, possibly, to reduce the number of variables. For example, it is possible to perform a principal component analysis of the subsequences of the set. Indeed, each extracted subsequence $T_{i,l}$ has length l corresponding to l measures of the number of cab rides in l consecutive time intervals. Correlations between these l measurements can be established.

The preprocessing allows one to determine a set of new variables that best explain the variability of measurements between different extracted subsequences. Thus, through preprocessing, each extracted subsequence $T_{i,l}$ is transformed into a subsequence, formed of up to l decorrelated values, or principal components, obtained from the original l measurements. Preprocessing may include normalization of the transformed subsequences to set their mean and standard deviation to predefined values. The normalization facilitates subsequent computer processing of the subsequences.

In this example, given the usual variations in road traffic as a function of time of day or day of week, the resulting time series T is likely to include recurring subsequences $T_{i,l}$. Thus, being able to correctly identify both recurrent subsequences corresponding to different types of normal traffic corresponding to different times of a typical day or week and unusual subsequences provides a general validation of the effectiveness of the proposed anomaly detection method compared to other, known, anomaly detection methods.

A sample of subsequences is selected, the sample ideally including all recurrent behaviors, hence all recurrent subsequences, of the time series T. To this end, some of the extracted subsequences are selected SEL $T_{i,l}$ (S3) and form a set of subsequences.

The selection can be for example random. Thus, a certain percentage r of subsequences $T_{i,l}$ of T is selected randomly (this percentage r being for example fixed at 20%). Such a selection mode offers no guarantee on the recurrence of the selected subsequences. However, for large time series, it is very likely that the selection made is representative of the real distribution of the different behaviors/subsequences. Experimentally, this hypothesis is verified. Moreover, the size of this selection is drastically smaller than the size of the time series T.

Alternatively, the selection can be performed on the basis of a discriminant criterion. A discriminant criterion based on a self-matching of the time series T can be defined as an example. For this purpose, the mathematical notions of empirical mean, standard deviation, distance, matching and self-matching are defined below in the context of time series.

The empirical mean of the time series T is given by $$\mu_y = \frac{\sum_{i=1}^{|T|} T_{i,1}}{|T|}.$$

The standard deviation of the time series is given by $$\sigma_y = \sqrt{\frac{1}{|T|-1} \sum_{i=1}^{|T|} (T_i - \mu_i)^2}.$$

The distance between two time series (noted A and B and of equal size) is given by $$dist(A, B) = \sqrt{\sum_{i=1}^{|A|} \left(\frac{A_{i,1} - \mu_A}{\sigma_A} - \frac{B_{i,1} - \mu_B}{\sigma_B}\right)^2}.$$

The matching between the two time series A and B is the result of computing $NN(A_{i,l},B)$ in B for each subsequence $A_{i,l}$ of A. Formally, $$B \bowtie_\ell A = [NN(A_{0,\ell}, B), NN(A_{1,\ell}, B), \ldots ,$$
$$NN(A_{|A|-\ell,\ell}, B)] = \left[\min_{x \in [0,|B|-\ell], x \neq 0} \{dist(A_{0,\ell}, B_{x,\ell})\},\right.$$
$$\left.\min_{x \in [0,|B|-\ell], x \neq 1} \{dist(A_{1,\ell}, B_{x,\ell})\}, \ldots , \min_{x \in [0,|B|-\ell], x \neq |A|-\ell} \{dist(A_{|A|-i,\ell}, B_{x,\ell})\}\right].$$

The self-matching of the time series T is the result of computing $NN(T_{i,l},T)$ in T for each subsequence $T_{i,l}$ of T. Formally, $T \bowtie_\ell T = [NN(T_{0,l},T), NN(T_{1,l},T), \ldots , NN(T_{|T|-l,l},T)]$.

In the discussed example of selection based on a discriminating criterion, the self-matching $S = T \bowtie_\ell T$ of the time series T is determined, and all subsequences $T_{i,l}$ satisfying the discriminant criterion $S_i < \in$ are selected, with E being a parameter fixed at the value $\in = \mu T \mu_{T \bowtie T}$. The subsequences thus selected have a nearest neighbor with a distance below the average. In other words, in this example, each subsequence thus selected has a degree of similarity, here a distance, exceeding a predetermined threshold, here an average distance, with at least one other subsequence in the set, here the nearest neighbor. This selection mode facilitates the presence of groups of similar subsequences, these groups being likely to be representative of the recurrences of the time series. However, this selection mode requires a quadratic computation time.

In addition, it may be provided to exclude EXCL $T_{i,l}$ (S31) from the selection certain subsequences. For example, if two sequences trivially overlap, then provision may be made to exclude one of these two subsequences. Thus, each subsequence whose proportion exceeding a predetermined threshold, is found in its entirety in at least one other subsequence is discarded from the selected set. For example, two subsequences $T_{i,l}$ and $T_{j,l}$ of T can be considered to trivially overlap if and only if $|i-j|<l/2$. Avoiding the selection of trivially overlapping subsequences ensures that the selected subsequences are recurrent across the entire time series T, thus potentially representative of the normal operation of the system of interest.

The aforementioned selection SEL $T_{i,l}$ (S3) and exclusion EXCL $T_{i,l}$ (S31) are independent and may be performed in any order or in conjunction.

As a result of the selection SEL $T_{i,l}$ (S3) and, if applicable, the exclusion EXCL $T_{i,l}$ (S31) of subsequences, a set of subsequences is obtained. This set can be realigned, for example, using a cross-correlation method or simple alignments of the maximum and minimum values. This realignment is non-discriminating and requires negligible computational time complexity with respect to the implementation of the entire anomaly detection method.

Figure 1:
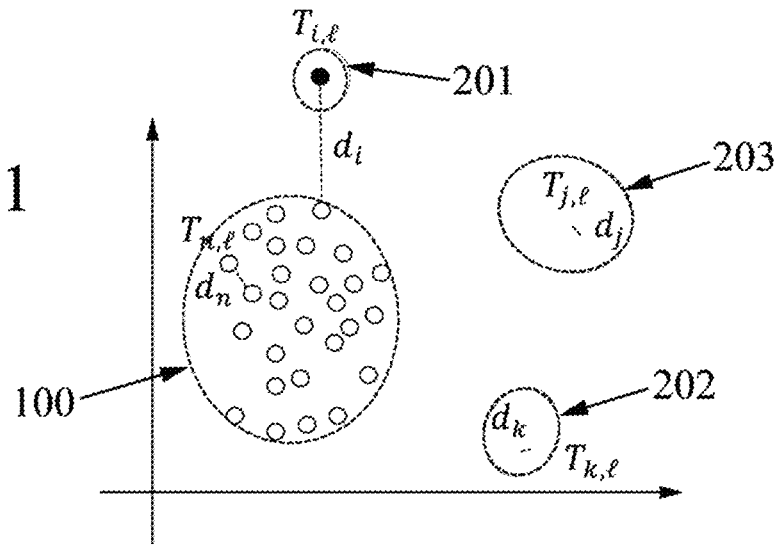
FIG. 1 graphically represents a known example of anomaly detection for an example subsequence distribution.
Figure 2:
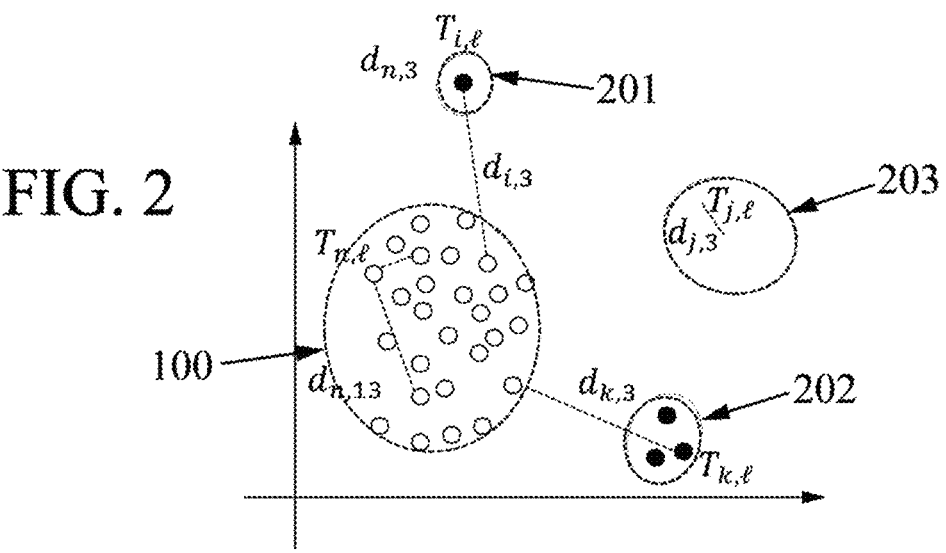
FIG. 2 graphically represents another known example of anomaly detection for an example subsequence distribution.
Figure 3:
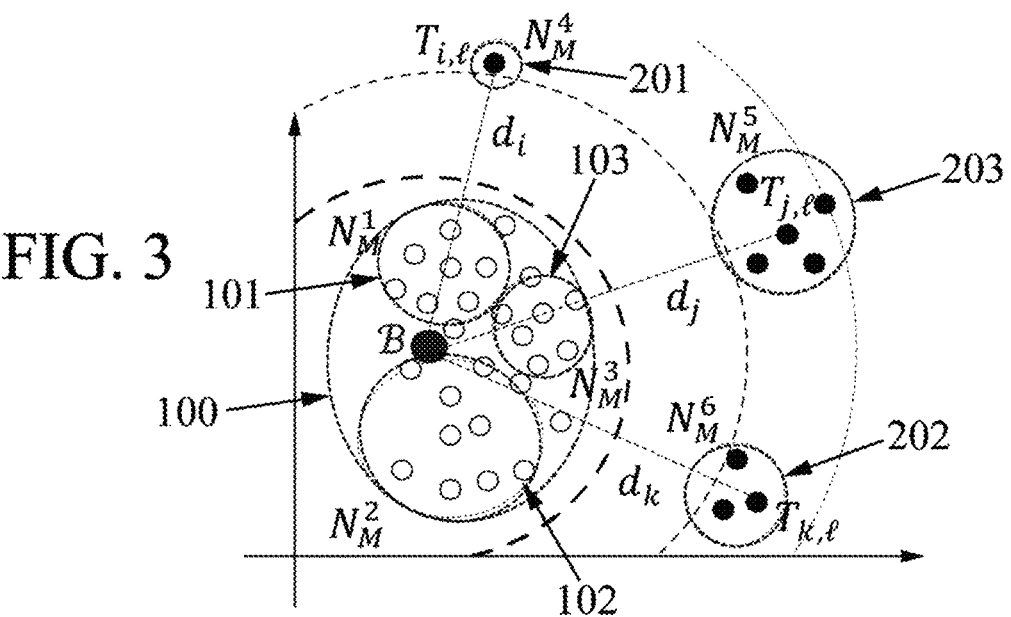
FIG. 3 graphically depicts an anomaly detection in a particular example embodiment, for the same example of subsequence distribution.

Reference is now made to FIG. 3, which schematically illustrates an example of the distribution of a set of subsequences selected from a plurality of subsequences extracted from the time series T. For simplicity, the subsequences of the set are normalized and represented in terms of two principal components. Thus, each subsequence of the set is represented by a point in an orthonormal reference frame of a plane. An advantage of this representation is that the smaller the Euclidean distance between two of these points, the more similar the two corresponding subsequences are. In general, the subsequences can be represented in a d-dimensional frame, where d denotes the number of principal components retained.

It is proposed to classify CLASS SEL (S4) the subsequences of the selected set into a plurality of subsequence groups based on at least one similarity criterion between each subsequence of the selected set and at least one reference subsequence.

In FIG. 3, six groups of subsequences are shown, namely, respectively:

three groups (101, 102, 103) corresponding to three different types of subsequences that can be identified as normal, whereby these three groups can be combined into a single group (100) that can be identified as a group of normal subsequences, and three groups (201, 202, 203), each group comprising a different number of subsequences, these three groups corresponding to three different types of subsequences that can be identified as abnormal.

Various known automatic classification methods, or "clustering", make it possible to identify these different groups of subsequences, without presuming the normality or abnormality of the groups thus formed or of the subsequences forming them.

Figure 4:
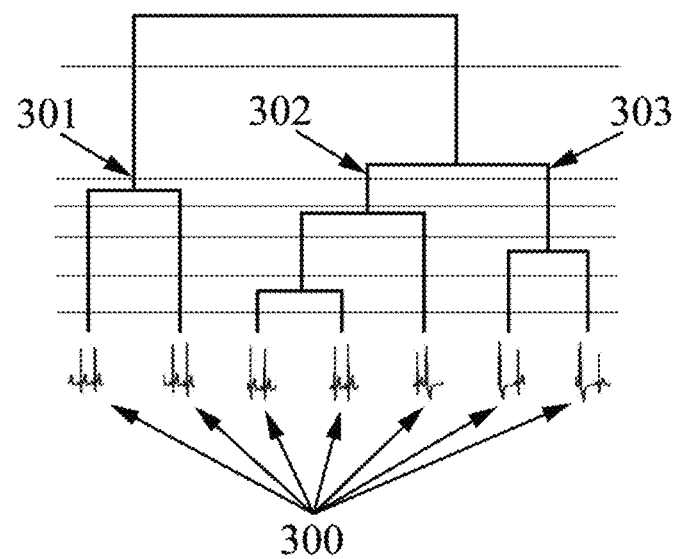
FIG. 4 represents a grouping of subsequences, in a particular example of an embodiment, in order to build a normal model of the operation of a system.

Reference is now made to FIG. 4, which schematically illustrates an example of a proposed automatic classification method. The classification is hierarchical here with a total coupling. The ranking is based on the notion introduced above of distance dist(A,B) between subsequences. More particularly, this distance corresponds, in this example, to the Euclidean distance between the points representing the different subsequences on FIG. 3.

The selected subsequences (300) can all be compared to each other to determine DET DEG (S41), for each pair of subsequences in the set, a degree of similarity. The two selected subsequences with the highest degree of similarity can be put together, forming FORM GRP (S42) a level 1 group. In this case, these are the two subsequences A and B with the lowest distance dist(A,B).

This level 1 group may be identified by a subsequence AB, generated GEN SS SEQ (S43) so as to be representative of the group and intermediate between subsequences A and B. In other words, according to a given principal component, the value of the AB subsequence is computable as intermediate between the corresponding value of the A subsequence and the corresponding value of the B subsequence. The values of the AB subsequence according to each principal component are computable as, for example, an average of the corresponding value of the A subsequence and the corresponding value of the B subsequence. Thus, the generated subsequence AB may be represented, in this example, by the midpoint of the segment connecting the points representing subsequences A and B.

The set of subsequences can be reduced RED ENS (S44) by replacing the pair of subsequences A and B forming the level 1 group with the subsequence AB representative of the level 1 group. Thus, after a first iteration, the set of subsequences is reduced by one, with a pair of subsequences being represented by a generated subsequence representing a level 1 group. The set thus comprises a level 1 group.

After a second iteration, the set of subsequences is reduced by a second unit, with another pair of subsequences being represented by a generated subsequence representing a level 2 group. The set thus includes a level 1 group and a level 2 group. Thus, if the subsequence set initially includes n subsequences, then after (n−1) iterations, the subsequence set is formed of (n−1) groups, i.e., one group of each level between 1 and (n−1), and each initially selected subsequence is included in one of the groups thus formed.

The coupling of all the initially selected subsequences to each other can thus be represented as an n-level dendrogram, from level 0 to level (n−1), the number of each level corresponding to the number of groups formed at that level. A total coupling, i.e. the implementation of (n−1) iterations in order to couple n sub-sequences initially selected, guarantees that downstream, the groups of sub-sequences obtained are necessarily adjacent and not superimposed. Two different groups obtained therefore necessarily correspond to two different behaviors of the system.

It is also possible to implement a partial coupling, i.e., either to stop the classification of the subsequences after i iterations so as to form i groups, i being less than (n−1), according to a stopping criterion, or, at the end of the total coupling, to determine a level i of cut of the dendrogram, so that the groups of level 1 to i are to be considered. In FIG. 4, a cut level 4, for example, groups a total number of seven subsequences into four groups, of levels 4 (301), 3 (302), 2 (303) and 1, respectively, with the level 1 group here being a subgroup of the level 3 group.

The value of i is determined according to a stopping criterion that can be predefined before the implementation of the algorithmic ranking method or determined iteratively by comparing different levels of the dendrogram.

In one example, the cut level i is chosen automatically based on the so-called "Minimum Description Length" principle. The description length of a subsequence refers to the total number of bits needed to encode the subsequence, which is also referred to as the entropy of the subsequence. This entropy is defined by $$H(T_{i,\ell}) = \sum_{i=1}^{\ell} P(T = T_{i,1}) \log_2 P(T = T_{i,1}).$$

The notation $P(T=T_{i,1})$ corresponds to the probability of finding the value $T_{i,1}$ in T.

The description length of the time series T is defined by $DL(T)=|T|*H(T)$ and quantifies the space required for storing the subsequence $T_{i,1}$. This value is minimal if the subsequence in question contains a maximum of similar values. In this case the compression of the bits reduces the storage space required. To simplify the calculations, the SAX (Symbolic Aggregate approXimation) representation of subsequences is used. Each subsequence of a group can be represented by its distance to the group center. The center of the group designates the generated subsequence, representative of the selected subsequences forming the group and intermediate to these selected subsequences. The smaller the respective distances between the center and each selected subsequence forming the group, the more optimal the clustering.

The conditional description length DL of a subsequence Ti,l quantifies the number of bits required to store that subsequence knowing the center of the group c to which it belongs. Formally, $DL(T_{i,l}|Center(c))=DL(T-Center(c))$. The conditional description length DLC of a group c quantifies the number of bits needed to store the subsequences of group c knowing the center of the group. Formally, $$DLC(c \mid \text{Center}(c)) = DL(\text{Center}(c)) + \sum_{d \in c} DL(d \mid \text{Center}(c)).$$

The unconditional description length of a group is defined by $DLC(c) = \sum_{d \in c} DL(d)$.

Considering a set of groups A (such as the one obtained after the selection of a level to cut the dendrogram), the bitsave measure can be applied to quantify the number of bits needed to store all the groups. This measure is defined by $$\text{bitsave}(A) = \sum_{c \in A} DLC(c) - DLC(c \mid \text{Center}(c)).$$

This measure is maximal when the intra-cluster similarity is maximal and when the number of clusters is minimal. It is thus possible to test each level iteratively (from the highest level to the lowest, and thus from the smallest number of clusters to the largest), and to stop the test when the bitsave measure stops growing, thus forming a final number of clusters corresponding to the number of the last level tested.

Thus, the selected set of subsequences can be classified into a relevant number of clusters, i.e., the different types of recurrent behaviors of the system of interest are represented by as many clusters. This classification is done automatically without the need to specify the number of relevant groups beforehand. The m constructed groups are respectively noted $c^1, \ldots, c^m$.

From the groups of sub-sequences formed, it is possible to construct CONST $N_M$ (S5), a normal model of the functioning of the system of interest.

In this normal model, each group ci of subsequences is represented by a subsequence representative of the subsequences of said group.

This representative subsequence is modeled MODEL $N_M^i$ (S51), or determined to be for example intermediate between the subsequences of said group. As mentioned above, each group $c^i$, formed as a result of the classification CLASS SEL (S4) using the minimum description length criterion, is stored with respect to its Center ($c^i$), i.e., with respect to the barycenter of the subsequences of said group. This barycenter may denote the modeled $N_M^i$ subsequence representing said group $c^i$.

In this normal model, each such modeled subsequence representative of a group $c^i$ is associated with a respective weight $w^i$, i.e., a respective contribution of the group. Thus, each group ci is represented, in the normal model, by a tuple $(N_M^i, w^i)$.

The weight $w^i$ is determined DET $w^i$ (S52) by comparing a collective distribution of the subsequences forming said group with a collective reference distribution. The advantage is that, by weighting the groups, it is possible to qualify more precisely the normal operation of the sensor over the entire time series, and thus to identify more precisely whether or not a given subsequence corresponds to an operating anomaly.

Specifically, each of the following criteria may be used, alone or in combination, to determine the weight of each group $c^i$:

the number $|c^i|$ of subsequences forming the group, the temporal coverage of the group (Coverage), and the centrality of the group (Centrality).

The temporal coverage of a given group (Coverage) is determined from the indices of the subsequences of the group. As a reminder, as specified above, each subsequence $T_{i,l}$ starts at index i, i.e., at the $i^{th}$ point in T, and contains the l points that follow. Specifically, it is possible to rely on the largest index among the indices of all subsequences in the group, known as the maximum index (MaxOffset), and the smallest index among the indices of all subsequences in the group, known as the minimum index (MinOffset). Formally, a possible determination, such that the greater the difference between the maximum and minimum index, the greater the temporal coverage, is Coverage($c^i$)=MaxOffset($c^i$)−MinOffset($c^i$).

The centrality of a group is determined from the distance between the center of the group and the centers of every other group. A possible determination is $$\text{Centrality}(c^i) = \frac{1}{(\sum_{x \in c^i} dist(\text{Center}(c^i), \text{Center}(x)))}.$$

Thus, the smaller the distances between the representative subsequence of a given group and the representative subsequences of other groups, the more central that given group is.

An example of a combination of criteria for determining the weight of a cluster may be the product of the square of the number of subsequences forming the cluster by the size of the portion of T covered by the cluster and the centrality of the cluster. Thus, in this example, the tuple $(N_M^i, w^i)$ is expressed as follows: $(N_M^i, w^i) = (\text{Center}(c^i), |c^i|^2 \cdot \text{Coverage}(c^i) \cdot \text{Centrality}(c^i))$.

In general, the normal model $N_M$ is defined by the tuples $(N_M^i, w^i)$ for each of the constructed groups, that is $N_M = \{(N_M^0, w^0), (N_M^1, w^1), \ldots, (N_M^m, w^m)\}$.

Referring to FIG. 3, six groups $c^1$ (101), $c^2$ (102), $c^3$ (103), $c^4$ (201), $c^5$ (203) and $c^6$ (202), can be constructed, and the normal model NM can be defined by six tuples $(N_M^1, w^1)$, $(N_M^2, w^2)$, $(N_M^3, w^3)$, $(N_M^4, w^4)$, $(N_M^5, w^5)$ and $(N_M^6, w^6)$, with the magnitudes $N_M^i$ denoting the centers of their respective ci groups and the magnitudes $w^i$ denoting the weights of their respective ci groups. By determining the arithmetic means of the coordinates of the $N_M^i$ centers of the constructed groups, weighted by their respective weights it is possible to obtain a barycenter B of the normal model.

Each extracted subsequence $T_{j,l}$ is then compared with the normal operating model, defined above, of the system of interest.

More particularly, a given subsequence may be compared with each modeled subsequence $N_M^i$ representative of a group ci in the normal model. The comparison may be a determination of a distance between the given subsequence and the representative subsequence.

Based on this comparison, it is possible to determine and attribute SCOR $T_{j,l}$ (S6) a normality score to this extracted subsequence.

For example, the normality score of a given subsequence may be obtained based on a comparison of the given subsequence with each subsequence of the normal model and based on a weighting of the results of said comparisons by the respective weights associated with each subsequence of the normal model.

Thus, the normality score of a given subsequence $T_{j,l}$ extracted from the time series T may denote the distance of that subsequence $T_{j,l}$ from the normal model, defined by:

$$d(T_{j,\ell}, N_M) = \sum_{N_M^i} w^i * \min_{x \in [0, \ell_{N_M} - \ell]} \{dist(T_{j,\ell}, N_{M_{x,\ell}}^i)\}.$$

This amounts to considering as the abnormality score of a given subsequence the distance between this given subsequence and the barycenter B of the normal operating model.

Based on the assigned normality scores, it is possible to identify ID $T_{k,l}$ (S7) at least one abnormal subsequence, indicating an abnormal operation of the system of interest.

For example, a subsequence with a large distance to the normal pattern may be considered abnormal. More formally, in this example, subsequence $T_{j,l}$ is less frequent (and thus more abnormal) than subsequence $T_{k,l}$ if $d(T_{j,l}, N_M) > d(T_{k,l}, N_M)$.

Based on at least one identified anomalous subsequence, it is further possible to determine DET SoH (S8) a health status of the system of interest.

A health status can be expressed as a scale of values, for example a percentage (0 to 100%), or in a binary form (healthy or not).

Figure 5:
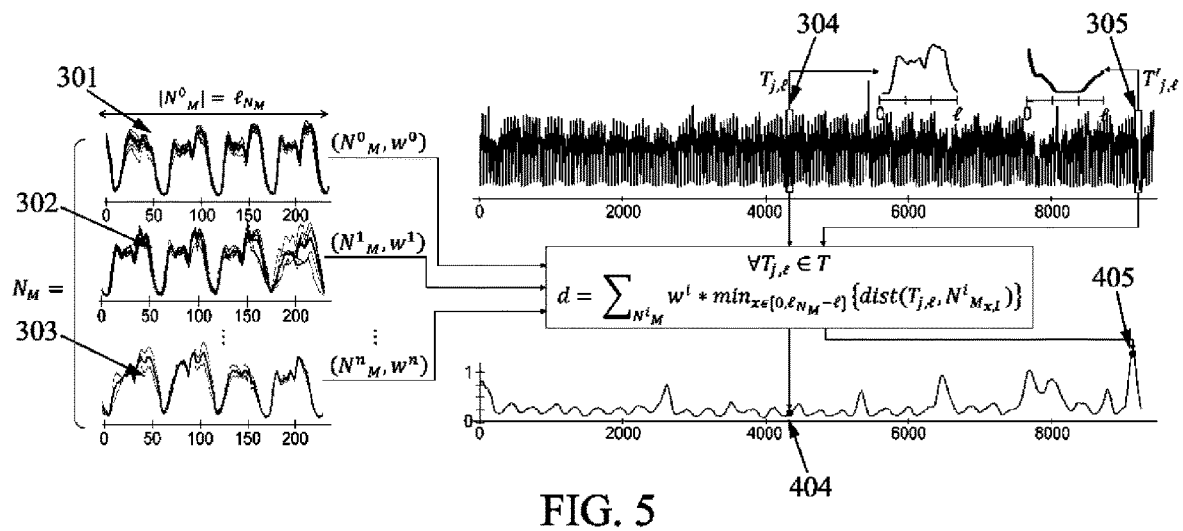
FIG. 5 represents, in a particular example of implementation, an anomaly detection of a system operation based on a comparison of subsequences with a normal operation model of said system.

Reference is now made to FIG. 5, which illustrates a method for detecting anomalies in the time series T of measurements of the number of cab rides provided per time interval. The detection is performed, as described above, by comparing extracted subsequences with a normal model $N_M$. The normal $N_M$ model is based on n groups constructed from a set of subsequences selected from the extracted subsequences. The $N_M$ normal model is formed by n tuples ($N_M^i$, $w^i$). Each tuple corresponds to one of the n constructed groups and is formed by a modeled subsequence (301, 302, 303) representative of said group and an associated weight.

A first subsequence $T_{j,l}$ (304) extracted from the time series T is compared to the normal model $N_M$, i.e., the distance of the first subsequence to the barycenter of the normal model is determined. By the comparison, a normalized abnormality score (404) is obtained. The lower the distance of the first subsequence to the barycenter of the normal model, the lower the value of this score. Here, we can visually see in FIG. 5 that the shape of the first subsequence (304) is close to those of some modeled subsequences (301) and (302) used to build the normal model. The determined abnormality score, here close to zero, confirms this observation and indicates a sufficient proximity with the normal model to consider the first subsequence as corresponding to a normal behavior of the system. Thus, the abnormality score indicates, for a considered instant of the system, a satisfactory status of health.

A second subsequence $T'_{j,l}$ (305) extracted from the time series T is compared to the normal model $N_M$. A normalized abnormality score (405) is thus obtained. Here, we visually notice in FIG. 5 that the shape of the second subsequence (305) does not match any of the modeled subsequences (301, 302, 303) used to construct the normal model. The value of this score, here greater than 1, confirms this observation and indicates a statistically abnormal distance from the normal model. The second subsequence is detected as corresponding to an abnormal behavior of the system. Thus, the abnormality score indicates, for a considered instant of the system, an insufficient status of health.

Figure 6:
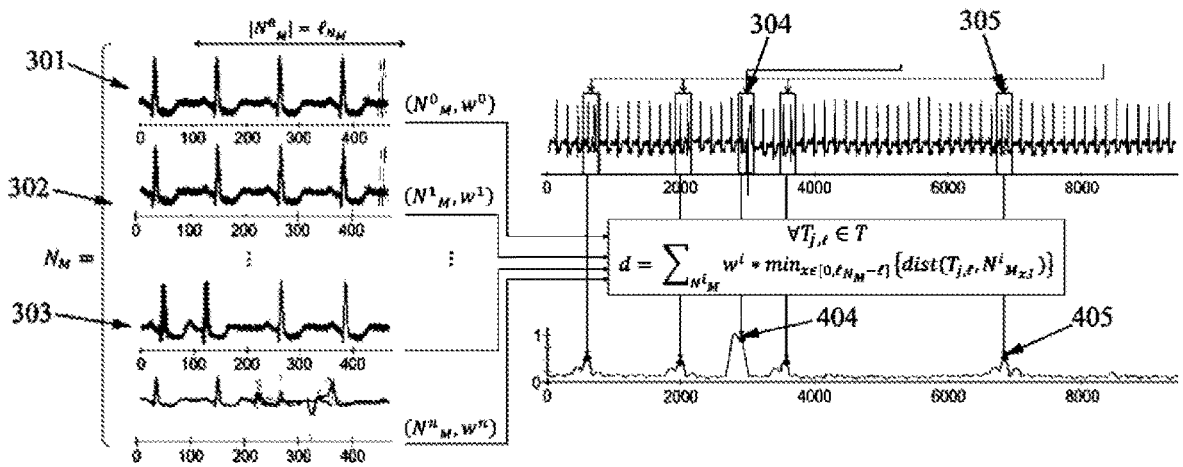
FIG. 6 represents, in another particular example of implementation, an anomaly detection of a system operation based on a comparison of sub-sequences with a normal model of operation of said system.
Figure 7:
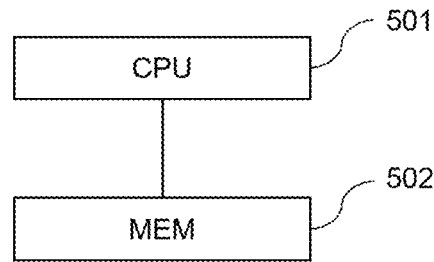
FIG. 7 schematically illustrates the structure of a processing circuit, in a particular example embodiment, for implementing the proposed determination method.

Reference is now made to FIG. 6, in which the system under consideration is a person and the sensor is an electrocardiograph. The time series T is an electrocardiogram of the person recorded over a time period of several hours. The constructed groups of subsequences (301, 302, 303) on which the normal model is based illustrate different typical, or recurrent, portions of the electrocardiogram, thus several recurrent series of heartbeats of the person. By comparing a large number of portions, or subsequences (304, 305), extracted from the electrocardiogram, with the normal model, it is possible to obtain for each of these portions an associated abnormality score. By automatic comparison of this abnormality score with a predefined threshold, it is possible to identify all the subsequences that deviate significantly from the normal model, thus constituting statistical anomalies, and thus being able to be considered as corresponding to a status of health that may require analysis by a practitioner. It is also possible to differentiate these statistically abnormal subsequences, on the basis of their abnormality score, into different types of abnormality. Thus, two abnormality scores (404, 405), although both above a threshold constituting a statistical abnormality, may be significantly different from each other and correspond to two different types of abnormality. It is then possible to identify each type of abnormality present on the electrocardiogram and to present, for example to a practitioner, an example of a sub-sequence extracted for each type identified. Although the association of a subsequence, a type of statistical anomaly, a specific status of health or any other quantity with a possible clinical picture is outside the scope of this document, the diagnosis of a practitioner is facilitated and accelerated in this case because the practitioner does not need to consult the entire electrocardiogram but, on the contrary, can immediately visualize extracts that are potentially relevant for the implementation of the diagnosis, because they correspond to the various statistical anomalies that may be present.

Many systems are equipped with sensors for measuring quantities indicative of their operation in the form of time series that are sequences of time-stamped values.

For example, in an industrial site, a pump is equipped with a flow sensor that reports the output speed of a fluid. In medicine, a patient may be equipped with an electrocardiograph to report cardiac activity (in particular, heart rate).

These systems can be equipped with processing circuit to store and execute the measurements locally. With the emergence of so-called intelligent and communicating systems, it is also possible to transmit the acquired measurements to a remote processing circuit for centralized processing. The processing of the acquired measurements can be used to qualify the operation of the system in question.

For example, considering as a system an industrial device that has to follow a pre-programmed temperature cycle and considering as an associated sensor a temperature probe, an objective can be to detect on the basis of temperature measurements by the sensor whether the industrial device is functioning correctly. Ideally, this detection is implemented automatically and without prior knowledge of the pre-programmed temperature cycle.

For example, considering a person or animal as a system and considering an electrocardiograph as an associated sensor, an objective may be to detect based on electrocardiograms whether the electrical activity of the heart of the person or animal is normal. Ideally, this detection is implemented automatically and unsupervised, including without first providing examples of normal electrocardiograms or electrocardiograms with abnormal characteristics.

Yet another example is that of connected objects, such as a smart factory where a sensor can measure a pressure or a temperature in a facility, or a connected vehicle whose behavior can be monitored, for example, by analyzing vibration data measured by a sensor.

An example of such a processing circuit, performing the measured data processing method described below. The processing circuit shown includes a CPU processor connected to a non-transitory recording medium MEM on which is recorded a program for carrying out a method as described below when that program is executed by the CPU processor.

It should be noted that, of course, in various industrial applications, many systems of interest are equipped with a plurality of sensors and configured to obtain a time series from each sensor. For example, a centrifugal pump is equipped with at least two pressure sensors (suction and discharge) and a flow sensor, all of which are absolutely necessary to determine its efficiency and thus quantify the proper functioning of the equipment. Although the determination method allows several time series to be analyzed, together or separately, it is considered in this example of implementation, for reasons of simplicity, the analyzing of a single time series in order to determine the health status of a system of interest.

In general, whatever the system of interest considered, the abnormal subsequences indicate the moments and the different types of anomalies detected by the sensor of the system of interest.

In an industrial system, this can be used to describe the health status of the system by symptoms (via alerts for example), and if necessary, to point out possible physical causes (degradation, wear and tear, unexpected event etc.).

Then, different actions can be taken, such as corrective actions (following a departure from the normal operating domain), repair actions (if these anomalies have had physical repercussions on the equipment), prediction/anticipation actions (if these anomalies have underlined degradation or wear, they can be taken into account during the next technical or maintenance interviews), and actions to enrich the feedback on the operation of the equipment In this way, the health status determined can be used to generate an alert indicating a potential failure of the system of interest, and/or to correct measurements subsequently received from the sensor and/or to predict a subsequent evolution of the health status of the system of interest and/or to feed a database of health statuses of systems of a type similar to the system of interest.

The invention claimed is:

1. A method of determining a health status of a system of interest equipped with at least one sensor, the method comprising:
   an acquisition OBT T of a time series formed of a sequence of measurements from the sensor as a function of time,
   an extraction EXTR $T_{i,\ell}$ of a plurality of subsequences from the time series, each extracted subsequence being formed of a plurality of measurements, consecutive in time, extracted from said sequence of measurements,
   a selection SEL $T_{i,\ell}$ of a set of subsequences, the set forming a part of the plurality of extracted subsequences,
   a classification CLASS SEL of the subsequences of the selected set, into several groups of subsequences, based on at least one similarity criterion between each subsequence of the selected set and at least one reference subsequence,
   a construction CONST $N_M$ of a normal operating model of the system of interest, the construction comprising, for each group of subsequences: a modeling MODEL $N_M^i$ of a subsequence representative of the subsequences of said group, and a determination DET $w^i$ of a weight associated with the modeled subsequence by comparing a collective distribution of the subsequences forming said group with a collective reference distribution, the normal operating model of the system of interest being defined by the modeled subsequences and the associated weights,
   an attribution SCOR $T_{j,\ell}$ of a normality score to each extracted subsequence, based on a comparison between said extracted subsequence and the normal operating model of the system of interest,
   an identification ID $T_{k,\ell}$ of at least one abnormal subsequence, indicating an abnormality in the functioning of the system of interest, based on the assigned normality scores, and
   based on said at least one identified abnormal subsequence, a determination DET SoH of the health status of the system of interest.

2. The method according to claim 1, comprising, in conjunction with the selection SEL $T_{i,\ell}$, an exclusion EXCL $T_{i,\ell}$ in which each subsequence with a proportion exceeding a predetermined threshold, is found in its entirety in at least one other subsequence, is excluded from the selected set.

3. The method according to claim 1, wherein the selection SEL $T_{i,\ell}$ is a random selection of subsequences among the plurality of subsequences.

4. The method according to claim 1, wherein the selection SEL $T_{i,\ell}$ is based on a comparison of the subsequences of the plurality of subsequences with each other, the set being formed such that each subsequence of the set has a degree of similarity exceeding a predetermined threshold with at least one other subsequence of the set.

5. The method according to claim 1, wherein the similarity criterion between a given subsequence A and a reference subsequence B results of:
   a determination of a distance dist(A,B) between the given subsequence and the reference subsequence, the distance dist(A, B) being defined as $$dist(A, B) = \sqrt{\sum_{i=1}^{|A|} \left( \frac{A_{i,1} - \mu_A}{\sigma_A} - \frac{B_{i,1} - \mu_B}{\sigma_B} \right)^2},$$

where $A_{i,1}$ and $B_{i,1}$ denote a first measurement in time, $\mu_A$ and $\mu_B$ denote a mean, and $\sigma_A$ and $\sigma_B$ denote a standard deviation of the first subsequence A and the second subsequence B respectively, and
   a comparison of the determined distance with a reference value.

6. The method according to claim 1, wherein the classification CLASS SEL is based on a hierarchical clustering of the subsequences in the set, the hierarchical clustering being performed by repeating the following steps until a stopping criterion is reached:
   determine DET DEG, for each pair of subsequences in the set, a degree of similarity,
   form FORM GRP a group of level i, where i represents the number of subsequences in the set, based on the similarity criterion so that the group of level i consists of the pair of subsequences in the set with the highest degree of similarity determined, generating GEN SS SEQ a subsequence representative of said level group i, intermediate between the subsequences of said level group i, and reducing RED ENS the set by replacing the pair of subsequences forming said level group i with the generated subsequence representative of said level group i.

7. The method according to claim 6, wherein:

during each iteration of the following steps, before performing each RED ENS reduction of the set, the subsequences forming the set are encoded and the total memory size of the encoded subsequences is determined, and the stopping criterion is based on a comparison of the determined for two consecutive iterations of the following steps.

8. The method according to claim 1, wherein during modeling MODEL $N_M^i$ of a subsequence representative of subsequences of said group, the modeled subsequence is intermediate between subsequences of said group.

9. The method according to claim 1, wherein the weight of each group is based on the number of subsequences forming said group.

10. The method according to claim 1, wherein the weight of each group is based on a temporal coverage of said group.

11. The method according to claim 1, wherein the weight of each group is based on a centrality of said group relative to several groups.

12. The method according to claim 11, wherein the normality score of a given subsequence is obtained based on a comparison of the given subsequence with each subsequence of the normal model and based on a weighting of the results of said comparisons by the respective weights associated with each subsequence of the normal model.

13. The method according to claim 1, wherein the system of interest is equipped with a plurality of sensors.

14. The method according to claim 1, wherein the system of interest is an industrial site with a set of sensors.

15. The method according to claim 14, wherein the industrial site has a sensor for temperature and/or a sensor for pressure.

16. The method according to claim 1, wherein the system of interest is a human or an animal with an integrated sensor.

17. The method according to claim 16, wherein the integrated sensor is an electrocardiograph.

18. A computer program comprising instructions for application of the method of claim 1 when said program is executed by a processor.

19. A device for non-transitory recording readable by a computer on which is recorded a program for the implementation of the method of claim 1 when such program is executed by a processor.

20. A processing circuit comprising a processor connected to the device for non-transitory recording of claim 19.

* * * * *